US00PP20991P2

(12) United States Plant Patent
Egger

(10) Patent No.: US PP20,991 P2
(45) Date of Patent: May 11, 2010

(54) ***AGASTACHE* PLANT NAMED 'COTTON CANDY'**

(50) Latin Name: ***Agastache* hybrid**
Varietal Denomination: Cotton Candy

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/383,649

(22) Filed: Mar. 27, 2009

(51) Int. Cl.
*A01H 5/00* (2006.01)

(52) U.S. Cl. ..... Plt./399

(58) Field of Classification Search ..... Plt./399
See application file for complete search history.

*Primary Examiner*—Kent L Bell
(74) *Attorney, Agent, or Firm*—Klarquist Sparkman, LLP

(57) ABSTRACT

A new and distinct form of *Agastache* plant characterized by medium size, light purplish pink flowers in narrow, tight clusters, purple calyces extending the flower color time for the plant, a low branching habit, a long bloom time, and excellent vigor.

1 Drawing Sheet

Botanical denomination: *Agastache* hybrid.
Variety designation: 'Cotton Candy'.

BACKGROUND OF THE INVENTION

The present invention relates to a new and distinct cultivar of *Agastache*, given the name, 'Cotton Candy'. *Agastache* is in the family Lamiaceae. The new cultivar is a F3 selection from a planned breeding program. The seed parent was *Agastache* 'Summer Love' (U.S. Plant Pat. No. 20,510). The pollen parent is unknown. Compared to *Agastache* 'Summer Love', the new variety has a shorter habit and lighter flower color.

This plant exhibits the following characteristics that make it unique:

1. medium size, light purplish pink flowers in narrow, tight clusters,
2. purple calyces extending the flower color time for the plant,
3. upright habit with low branching,
4. a long bloom time, and
5. excellent vigor.

The new variety has been reproduced only, by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a group of nine-month-old *Agastache* 'Cotton Candy' growing in the field in late summer in Canby, Oreg.

DETAILED PLANT DESCRIPTION

The following is a detailed description of the new *Agastache* cultivar based on observations of a nine-month-old specimen grown outside in the ground in the trial beds in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Upright, spreading herbaceous perennial.
*Cold hardiness.*—USDA Zone 7–9.
*Size.*—Grows to 45 cm wide and 65 cm tall to the top of the flowers.
*Vigor.*—Excellent.
*Stem.*—Square, grows to 4 mm wide and 35 cm tall, uncinate, internodes average 4.5 cm long, Yellow Green 147B.
*Roots.*—White 155B, fibrous, plants root easily from stem tip cuttings.

Leaf:

*Type.*—Simple.
*Arrangement.*—Opposite.
*Shape.*—Ovate to deltoid.
*Venation.*—Pinnate.
*Margins.*—Crenate.
*Apex.*—Acute.
*Base.*—Truncate.
*Blade size.*—Grows to 4 cm long and 3 cm wide.
*Surface texture.*—Very short, uncinate hairs on both sides.
*Petiole description.*—2 cm long and 1.2 mm wide, pubescent, Yellow Green 147B.
*Leaf color.*—Top side Yellow Green 147A, bottom side Yellow Green 147B.

Inflorescence:

*Type.*—Terminal spike with 11 to 19 dense whorls.
*Number of flowers.*—Up to 300 per spike.
*Peduncle.*—2 cm to 5 cm tall and 1.5 mm wide, pubescent, Yellow Green 147B.
*Pedicel.*—1 mm to 2 mm long, pubescent, Yellow Green 147B.
*Bloom period.*—June through frost in Canby, Oreg.

Flower bud:

*Size.*—12 mm long and 3 mm wide at the widest point prior to opening.

*Description.*—Tubular.

*Surface texture.*—Pubescent.

*Color.*—Greyed Orange 174D.

Flower:

*Type.*—Zygomorphic.

*Shape.*—Bilabiate, tubular.

*Size.*—2 cm long and 6 mm wide.

*Corolla description.*—17 mm long and spreads to 6 mm wide, color inside and outside Purple 75D, pubescent outside and glabrous inside, tube 12 mm long and 1 mm to 3 mm wide; 2 upper lobes joined 2 mm long and 2.5 mm wide, ovate, acute, entire; three lower lobes, two spreading sideways, each 1.5 mm long and 2 mm wide, obtuse, entire; the bottom lobe broad, reflexed, obovate, obtuse, entire; 3 mm wide and 2.4 mm deep.

*Calyx description.*—10 mm long and 2.5 mm wide, color Yellow Green 147C on bottom half to Purple 77A on top half, pubescent outside and glabrous inside, 5 lobed, lobes narrow, 2 mm long, entire, acuminate.

*Pistil description.*—25 mm long, ovary 0.5 mm long, Yellow Green 146C, style 24.5 mm long, stigma and style Red Purple 69D.

*Stamen description.*—4 in number, paired, exerted and reflexed, filaments 9 mm long, Violet 84A, anthers 1 mm long, Purple 77D, pollen White 155D.

*Fragrance.*—Herbal.

*Lastingness.*—A spike blooms for about 3 weeks on the plant.

Fruit: 4 nutlets, Green 144A.

Seed: Oblong, 1.5 mm long, Black 202A, low fertility.

Pests and diseases: *Agastache* are known to be susceptible to mildew and rust in dry summer months. The new cultivar has no known resistances but has shown no problems in Canby, Oreg.

I claim:

1. A new and distinct cultivar of *Agastache* plant substantially as shown and described.

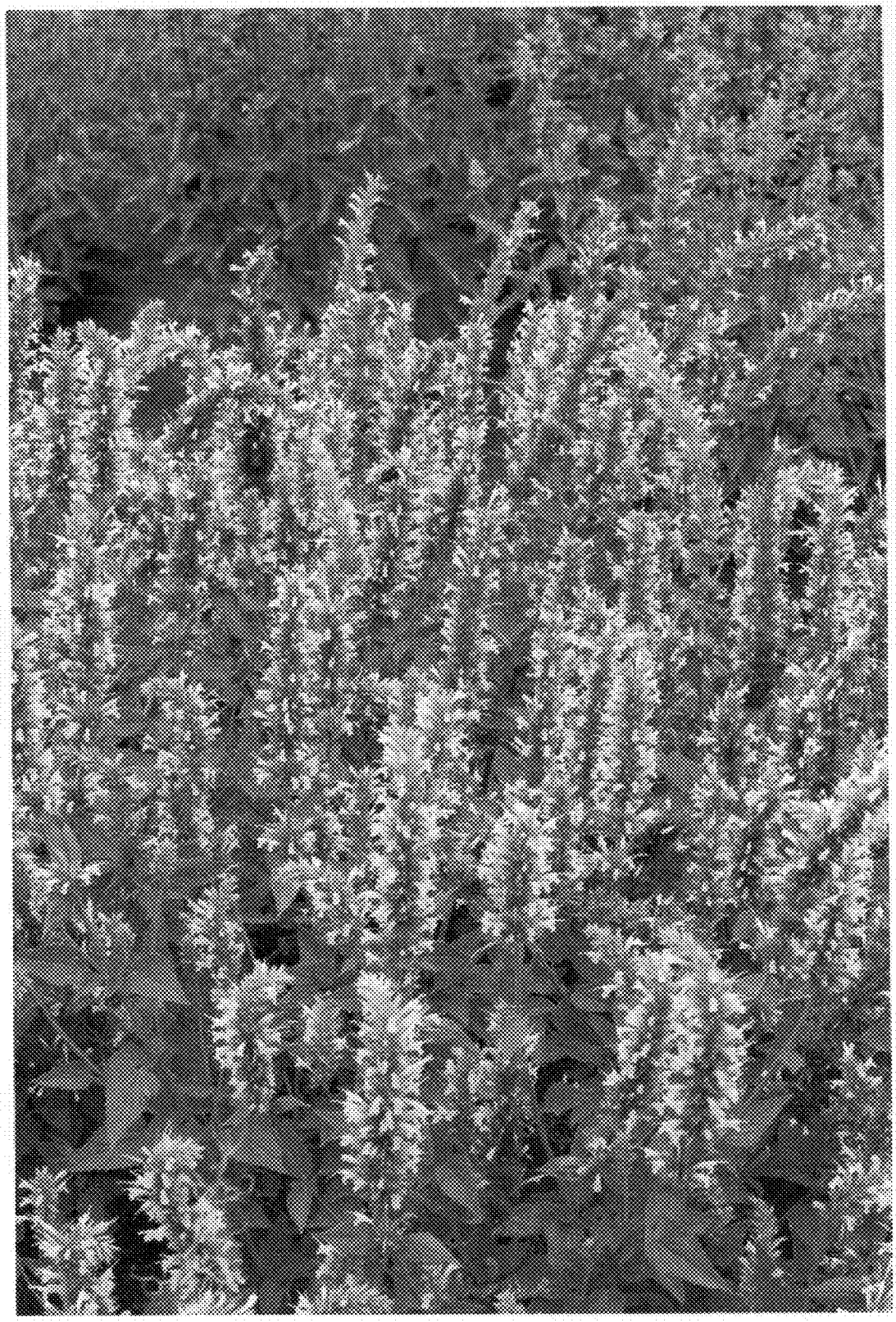

* * * * *